(12) United States Patent
Nguyen et al.

(10) Patent No.: US 6,440,456 B1
(45) Date of Patent: *Aug. 27, 2002

(54) AQUEOUS CARRIER SYSTEMS FOR LIPOPHILIC INGREDIENTS

(75) Inventors: Nghi Van Nguyen, Edison, NJ (US); David W. Cannell, New York, NY (US)

(73) Assignee: L'Oreal S.A., Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/328,785

(22) Filed: Jun. 9, 1999

(51) Int. Cl.$^7$ .......................... A61K 9/127; A61K 7/00; A61K 7/06

(52) U.S. Cl. ............... 424/450; 424/401; 424/70.1; 424/70.2; 424/70.11; 424/70.21; 424/70.22; 424/73; 514/881; 514/937

(58) Field of Search ................. 424/401, 450, 424/70.1, 70.2, 70.11, 70.21, 70.22, 73; 514/881, 937

(56) References Cited

U.S. PATENT DOCUMENTS

| | | | |
|---|---|---|---|
| 4,174,296 A | | 11/1979 | Kass |
| 4,389,418 A | | 6/1983 | Burton |
| 4,562,214 A | | 12/1985 | Barker et al. |
| 4,690,774 A | | 9/1987 | Vishnupad et al. |
| 4,788,011 A | | 11/1988 | Busse et al. |
| 4,826,828 A | | 5/1989 | Wilmott et al. |
| 4,832,858 A | | 5/1989 | Vishnupad et al. |
| 4,832,872 A | | 5/1989 | Scandel |
| 4,874,553 A | | 10/1989 | Hager et al. |
| 4,980,084 A | | 12/1990 | Vishnupad et al. |
| 5,002,761 A | | 3/1991 | Mueller et al. |
| 5,160,739 A | * | 11/1992 | Kampe |
| 5,173,303 A | | 12/1992 | Lau et al. |
| 5,308,526 A | | 5/1994 | Dias et al. |
| 5,310,556 A | | 5/1994 | Ziegler |
| 5,312,559 A | | 5/1994 | Kacher et al. |
| 5,496,488 A | | 3/1996 | Kacher et al. |
| 5,674,511 A | | 10/1997 | Kacher et al. |
| 5,716,920 A | | 2/1998 | Glenn, Jr. et al. |
| 5,783,554 A | * | 7/1998 | Li |
| 5,804,540 A | | 9/1998 | Tsaur et al. |
| 5,858,938 A | | 1/1999 | Glenn, Jr. et al. |
| 5,885,948 A | | 3/1999 | Glenn, Jr. et al. |

FOREIGN PATENT DOCUMENTS

| | | |
|---|---|---|
| BE | 895 719 A1 | 7/1983 |
| EP | 0 103 911 | 3/1984 |
| EP | 0 123 071 A2 | 10/1984 |
| EP | 0 340 592 A2 | 11/1989 |
| EP | 0 521 799 A1 | 1/1993 |
| EP | 596 465 A1 | 5/1994 |
| EP | 0 868 898 A1 | 10/1998 |
| EP | 872 229 A1 | 10/1998 |
| EP | 897 718 A2 | 2/1999 |
| WO | WO 96/12469 | 5/1996 |
| WO | 96/25144 | 8/1996 |
| WO | WO 98/56333 | 12/1998 |

OTHER PUBLICATIONS

English Translation of EP 0 897 718, previously submitted.
Ribosa et al., "Physico–chemical Modifications of Liposome Structures Through Interaction With Surfactants," *International Journal of Cosmetic Science,* pp. 131–149 (1992).
Copy of International Search Report dated Nov. 15, 2000.

* cited by examiner

Primary Examiner—Gollamudi S. Kishore
(74) Attorney, Agent, or Firm—Finnegan, Henderson, Farabow, Garrett & Dunner LLP

(57) ABSTRACT

A composition containing at least one organic phospholipid capable of forming bilayers in aqueous solution; at least one amphoteric surfactant; at least one nonionic surfactant present in an amount by weight equal to or greater than the amount of the phospholipid; at least one suspending agent present in an amount effective for maintaining a stable composition; and a lipophilic ingredient. The invention also relates to a delivery system for lipophilic ingredients containing the above components, and an aqueous phase, wherein the organic phospholipid, amphoteric surfactant, and nonionic surfactant are present in a combined amount sufficient to allow the lipophilic ingredient to be incorporated into the system. A method of treating akeratinous substance is also disclosed.

63 Claims, No Drawings

AQUEOUS CARRIER SYSTEMS FOR LIPOPHILIC INGREDIENTS

The present invention relates to novel carrier systems based on organic phospholipids capable of forming bilayers in aqueous solution, nonionic surfactants, amphoteric surfactants and suspending agents, wherein these carrier systems allow lipophilic materials to be incorporated into aqueous solutions.

Organic phospholipids play an important role in the cosmetics and pharmaceutical industries because of their outstanding physiological properties, such as, for example, emulsifying, softening, and anti-oxidant effects. When hydrolyzed, organic phospholipids yield phosphoric acid, an alcohol, a fatty acid, and a nitrogenous base. Most phospholipids are amphipathic, i.e., have polar "heads" and non-polar "tails." As a result, most phospholipids tend to arrange spontaneously into a bilayer when suspended in an aqueous environment, with the polar heads contacting the water and the non-polar tails contacting each other. Most naturally occurring phospholipids prefer to form vesicular bilayers in water solutions. In such a bilayer vesicle, no non-polar part of the phospholipid has any contact with the water solution.

Because of their non-polar portions, phospholipids typically are water-insoluble and incompatible with many water soluble anionic compounds, such as anionic surfactants. While they can be solubilized in water at low levels by a range of surfactants, this is often not easily accomplished.

Instead, solubilization has been accomplished conventionally using specific solubilizing agents in aqueous alcoholic solutions. For example, U.S. Pat. No. 4,874,553 to Hager et al. discusses methods of rendering phospholipid mixtures water-soluble or water-dispersible by using certain amine compounds as solubilizing agents. U.S. Pat. No. 4,174,296 to Kass describes a method of improving the solubility of phospholipid compounds in water, in particular lecithin compounds, by mixing lecithin with specific single solubilizing agents, including amphoteric and anionic surfactants. These methods utilize alcohol for cosolubilization. Alcohol solutions can have the drawback of disrupting any bilayer formation by altering the solution such that the alcohol functions as a secondary solvent.

Lecithins and other phospholipids have been used in the pharmaceutical industry to formulate carriers for water-insoluble drugs. For instance, in U.S. Pat. No. 5,173,303 to Lau et al., water-insoluble material is encapsulated by vesicles composed of phospholipids such as lecithin. Ribosa et al., in "Physico-chemical modifications of liposome structures through interaction with surfactants,"0 Int'l Journal of Cosmetic Science 14:131–149 (1992), also discuss solubilization of phospholipids via the interaction of liposomes with surfactants. Lau and Ribosa, however, investigated only dilute solutions of pure liposomes.

Despite difficulties in solubilization, certain organic phospholipids, such as lecithin, can advantageously give hair and skin a soft, moisturized feel because they have a strong affinity for the hydrophobic surface of the hair and skin. In addition, lipophilic ingredients, including hydrocarbons such as petrolatum, offer moisturizing and protecting properties that are also desirable in many applications including hair care and skin care. However, in addition to the difficulties encountered in solubilizing phospholipids, the incorporation of high concentrations or "loads" of lipophilic ingredients into an aqueous environment has proven difficult. The water-insoluble nature of the these ingredients has made their utilization in aqueous environments complicated.

It would thus be desirable for cosmetic and pharmaceutical applications to provide delivery systems that include such organic phospholipids as carriers for high loads of other lipophilic ingredients, without the need for alcohols and other similar solvents.

For the most part, the use of hydrocarbons such as petrolatum in hair care and skin care has been accomplished through the use of water-in-oil emulsions, encapsulating lipids and other multi-phase compositions. For example, U.S. Pat. No. 5,716,920 to Glenn et al. describes a method of making a liquid personal cleaning composition that contains a lipophilic skin moisturizing agent such as hydrocarbon oils and waxes by the use of an encapsulation technique. However, the methods described result in a multi-phase emulsion or composition comprised of droplets.

Thus, there remains a need for an aqueous delivery system that can solubilize and/or form a stable suspension (i.e., without phase separation) with lipophilic materials such as hydrocarbons, waxes, and silicones, where these lipophilic materials will remain stable and/or not precipitate out of solution, where the amount of deposition of lipophilic material can be controlled, and where the system could carry other ingredients in addition to the lipophilic ingredient. For example, it would be beneficial to have a system which incorporates lipophilic materials into compositions containing other ingredients, such as dyeing and permanent wave compositions. The present invention provides such a delivery system.

To achieve these and other advantages, the present invention is drawn to a composition made up of at least one organic phospholipid capable of forming bilayers in aqueous solution, at least one amphoteric surfactant, at least one nonionic surfactant, and at least one suspending agent or viscosity increasing agent. The nonionic surfactant is present in an amount equal to or greater than the amount of the organic phospholipid. The suspending agent is present in an amount effective for maintaining a stable composition. A stable composition or system is one that experiences substantially no settling out or phase separation.

In another embodiment, the present invention relates to an aqueous delivery system for lipophilic materials. The delivery system (or "carrier") includes the above-described composition in addition to at least one lipophilic ingredient, and an aqueous phase. The nonionic surfactant preferably is present in an amount equal to or greater than the amount of the organic phospholipid. The organic phospholipid, the amphoteric surfactant, and the nonionic surfactant are present in a combined amount sufficient to allow the lipophilic ingredient to be incorporated into the delivery system by the composition of the present invention. The suspending agent is present in an amount effective for maintaining a stable delivery system, i.e. one that experiences substantially no settling out or phase separation.

In a preferred embodiment, the delivery system of the present invention results in a stable, milky suspension, solution, lotion, or cream. A delivery system comprising at least one organic phospholipid capable of forming bilayers in aqueous solution, at least one amphoteric surfactant, at least one nonionic surfactant, at least one water-insoluble ingredient, and an aqueous phase has been described previously. See WO 98/56333. This system is referred to as the "LAN" because it preferably contains a lecithin (L) as the phospholipid, an amphoteric surfactant (A), and a nonionic surfactant (N). The LAN system previously described "solubilized" a water-insoluble ingredient resulting in a clear or cloudy solution. However, the LAN system of the present invention is different in that, by containing a suspending or viscosity increasing agent, it enables a lipophilic ingredient to be incorporated into the system to give a stable, milky suspension, solution, lotion, or cream.

A milky solution is not equivalent to a cloudy solution. For example, a cloudy solution is a solution that contains small particles, is turbid, will experience settling over time and/or will experience separation/precipitation of phases. The stable milky solution of the present invention generally does not settle over time and typically, experiences no separation of phases. Like the previously disclosed LAN clear solution system, the milky LAN system of the present invention will incorporate or act as a carrier for lipophilic materials. However, the LAN system of the present invention, with the inclusion of a suspending agent, offers the advantage of being able to incorporate a larger amount or higher weight of lipophilic material per weight of the entire composition than the LAN system of WO 98/56333. Additionally, the LAN system of the present invention can be a more effective carrier of hydrocarbons, such as petrolatum and polyethylenes; waxes, such as Beeswax; and silicones.

The stable, milky LAN system of the present invention may be either a solution, suspension, lotion, or cream. Regardless of their form, the milky solutions, lotions, creams, or suspensions remain stable without substantial settling or substantial separation of phases. It is the viscosity of the resulting milky LAN system that will determine whether the composition is a solution, suspension, lotion, or cream.

The present invention is also drawn to a process for the preparation of the milky aqueous system comprising: (a) combining at least one organic phospholipid capable of forming bilayers in aqueous solution, at least one amphoteric surfactant, at least one nonionic surfactant, at least one lipophilic ingredient, and water, (b) stirring the combined ingredients of (a) while heating, (c) adding an appropriate amount of a suspending agent and stirring while heating, and (d) cooling the resulting solution.

Finally, in yet another embodiment, the present invention is drawn to a method for treating keratinous substances such as hair, skin, or eyelashes. First an aqueous solution is prepared containing at least one organic phospholipid capable of forming bilayers in aqueous solution; at least one amphoteric surfactant; at least one nonionic surfactant present in an amount by weight equal to or greater than the amount of the phospholipid; and at least one lipophilic ingredient. The phospholipid, amphoteric surfactant, and nonionic surfactant are present in a combined amount sufficient to allow the lipophilic ingredient to be incorporated into a stable aqueous system. A suspending agent, in an amount effective for maintaining a stable system, is subsequently added to the aqueous system. The resulting stable milky system is then applied to the keratinous substances.

Reference will now be made in detail to the present preferred embodiment(s) of the invention.

Advantageously, the present invention allows lipophilic materials or ingredients to be incorporated into an aqueous system to give a stable, milky solution, lotion, cream, or suspension. No alcohol is required for cosolubilization, and there is no need for liposome preparation. Further, when the water evaporates, the residue left behind includes the lipophilic material and/or the phospholipid. The composition of the invention is also easy to formulate and is gentle on the hair, skin, or eyelashes when the surfactants used are mild.

The compositions and delivery systems of the present invention readily deposit the organic phospholipid/lipophilic substances on the hair, skin, and eyelashes, and, because of their inherent insolubility, resist being washed off with water. Accordingly, these compositions and delivery systems can be used in hair shampoos, conditioners, hair dyeing compositions, including oxidative dyes and bleaches, permanent waving compositions, curl relaxing compositions, hair setting compositions, bath and body products, sunscreens, or cosmetics such as mascaras and foundations.

Additionally, the "load" carried by these systems can be quite high, a benefit that inures both to the user and to the manufacturer in an economic sense. Load is defined as the weight of added hydrophobe (lipophilic material) divided by the weight of the phospholipid expressed as a percentage. Thus, 1 g of hydrophobe in a composition with 5 g phospholipid is a ⅕ or 20% load. In the art, 50% is considered a high load and can be achieved with certain hydrophobes and surfactant combinations. In the present invention, loads of greater than 100% are possible. In other words, stable solutions, lotions, and creams that contain more hydrophobe than phospholipid can be obtained. For example, one preferred method of the present invention results in stable creams comprising 50 times more petrolatum than phospholipid.

Without being bound to a particular theory, the inventors believe that in the composition of the present invention an organized structure, likely a laminar gel, is formed between the organic phospholipid and the nonionic surfactant and is solubilized by the amphoteric surfactant. The organized structure can incorporate other water-insoluble materials or hydrophobes. In aqueous systems, the structure remains organized. The suspending agent helps to maintain a stable system. The result is a stable milky system as evidenced by the lack of substantial settling out or substantial separation of phases.

In one embodiment, therefore, the invention is drawn to a composition comprising at least one organic phospholipid capable of forming bilayers in aqueous solution, at least one amphoteric surfactant, at least one nonionic surfactant, and at least one suspending agent, where the nonionic surfactant is present in an amount by weight equal to or greater than the amount of the phospholipid and the suspending agent is present in an amount effective for maintaining a stable system. Neither the amphoteric nor the nonionic surfactant alone will give a satisfactory solution with the organic phospholipids.

With respect to the ingredients of the inventive composition, the preferred organic phospholipids capable of forming bilayers in aqueous solution are lecithins. Lecithins are mixtures of phospholipids, i.e., of diglycerides of fatty acids linked to an ester of phosphoric acid. Preferably, lecithins are diglycerides of stearic, palmitic, and oleic acids linked to the choline ester of phosphoric acid. Lecithin is usually defined either as pure phosphatidyl cholines or as crude mixtures of phospholipids which include phosphatidyl choline, phosphatidyl serine, phosphatidyl ethanolamine, phosphatidyl inositol, other phospholipids, and a variety of other compounds such as fatty acids, triglycerides, sterols, carbohydrates, and glycolipids.

The lecithin used in the present invention may be present in the form of a liquid, powder, or granules. Lecithins useful in the invention include, but are not limited to, soy lecithin and hydroxylated lecithin. For example, ALCOLEC S is a fluid soy lecithin, ALCOLEC F 100 is a powder soy lecithin, and ALCOLEC Z3 is a hydroxylated lecithin, all of which are available from the American Lecithin Company.

Other than lecithins, another group of phospholipids which may be useful in the present invention are multifunctional biomimetic phospholipids. For example, the following multifunctional biomimetic phospholipids manufactured by Mona Industries may be useful: PHOSPHOLIPID PTC, PHOSPHOLIPID CDM, PHOSPHOLIPID SV, PHOSPHOLIPID GLA, and PHOSPHOLIPID EFA.

The amphoteric surfactants useful in the present invention include, but are not limited to, betaines, sultaines, hydroxysultaines, alkyl amphodiacetates, alkyl amphodipropionates, and imidazolines, or salts thereof. It is recognized that other fatty acid condensates such as those formed with amino acids, proteins, and the like are suitable. Amphoteric surfactants are typically available for commercial sale in solution form with the active surfactant accounting for approximately 40% of the total solution weight. Cocamphodipropionate is particularly preferred, for example, MIRANOL C2M-SF Conc. (disodium cocamphodipropionate), in its salt-free form, available from Rhône-Poulenc. MIRANOL is sold in solution form with amphoteric surfactants composing approximately 40% of the total solution weight; for example, 10 g of MIRANOL contain about 4g of amphoteric surfactant. Also preferred is CROSULTAINE C-50 (cocamidopropyl hydroxysultaine), available from Croda. CROSULTAINE is also sold in solution form with the amphoteric surfactant composing approximately 50% of the total solution weight. Other amphoteric surfactants useful in the present invention include disodium wheatgermimido PEG-2 sulfosuccinate, available under the trade name MACKANATE WGD from McIntyre Group Ltd., which is a solution with amphoteric surfactants composing approximately 39% of the total solution weight, and disodium soyamphodiacetate, available under the trade name MACKAM 2S from McIntyre Group Ltd., which is a solution with amphoteric surfactants composing approximately 34.5% of the total solution weight.

The nonionic surfactants useful in the present invention are preferably formed from a fatty alcohol, a fatty acid, or a glyceride with a $C_8$ to $C_{24}$ carbon chain, preferably a $C_{12}$ to $C_{18}$ carbon chain, more preferably a $C_{16}$ to $C_{18}$ carbon chain, derivatized to yield a Hydrophilic-Lipophilic Balance (HLB) of at least 10. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 10. Preferably the nonionic surfactants contain ethoxylate in a molar content of from 10–25, more preferably from 10–20 moles.

Nonionic surfactants may be selected from, but are not limited to, the following:

| # of C's | Name | Trade Name |
|---|---|---|
| C-12 | Laureth-23 | BRIJ 35, available from ICI Surfactants |
| C-16 | Ceteth-10 | BRIJ 56, available from ICI Surfactants |
| C-16 | Ceteth-20 | BRIJ 58, available from ICI Surfactants |
| C-16 | IsoCeteth-20 | Arlasolve 200, available from ICI Surfactants |
| C-18 | Steareth-10 | Volpo S-10, available from Croda Chemicals Ltd. |
| C-18 | Steareth-16 | Solulan-16, available from Amerchol Corp. |
| C-18 | Steareth-20 | BRIJ 78, available from ICI Surfactants |
| C-18 | Steareth-25 | Solulan-25, available from Amerchol Corp. |
| C-18= | Oleth-10 | BRIJ 97, available from ICI Surfactants |
| C-18= | Oleth-20 | Volpo-20, available from Croda Chemicals Ltd. |

Alkyl polyglucose surfactants sold under the name PLANTAREN, available from Henkel, may also be used.

One of ordinary skill in the art may vary the suspending agent or viscosity increasing agents, both of which are referred to as a suspending agent herewith, based on the specific content of the LAN delivery system, including the lipophilic material being employed. Any suspending agent that is unreactive and/or will not form a complex that results in substantial phase separation with the organic phospholipid, the amphoteric surfactant, the nonionic surfactant, or the lipophilic ingredient is useful in the present invention. Thus, some suspending agents that are useful in some LAN delivery systems may not be useful in all LAN delivery systems. Suspending agents useful in the practice of the invention include, but are not limited to, biopolymers such as sclerotium gum available as AMIGEL from Alban Muller; polysaccharide gums such as hydroxyethylcellulose available as CELLOSIZE from Amerchol; polyacrylamides such as SEPIGEL 305 available from SEPPIC; stearates such as PEG-150 pentaerythrityl tetrastearate available as CROTHIX from Croda, and inorganic clays such as Bentonite.

In one preferred embodiment of the composition of the present invention, the organic phospholipid capable of forming bilayers in aqueous solution, the amphoteric surfactant, and the nonionic surfactant are present in the composition such that the nonionic surfactant is present in an amount by weight greater than the amount of phospholipid. In a more preferred embodiment, the amount of phospholipid in the composition is kept fixed while the amounts of the amphoteric and nonionic surfactants are increased.

In a still more preferred embodiment, calculating the phospholipid as present at a value of 1, the phospholipid, amphoteric surfactant and nonionic surfactant are preferably present in the composition in a ratio of about 1:0.8:2 and above by weight, i.e., where the amounts of the surfactants can be increased independently of each other but the amount of phospholipid stays fixed. The ratio is considered to be "above" 1:0.8:2 when the amount of either of the surfactants increases. When the phospholipid/amphoteric/nonionic system is employed as a carrier for a lipophilic material, the ratio is preferably about 1:1.2:2 and above and even more preferably about 1:1.6:2. The loading capability for lipophilics carried by the delivery system of the present invention may be maximized if the ratio of nonionic surfactant to phospholipid is minimized, with the bilayers still being solubilized, because an excess of nonionic surfactant may disrupt the organized structure.

In one preferred embodiment, the composition of the present invention comprises ALCOLEC S (soy lecithin), MIRANOL C2M-SF Conc. (disodium cocamphodipropionate, an amphoteric surfactant), ARLASOLVE 200 (IsoCeteth-20, a nonionic surfactant) in a ratio of 1:4:2 (which is a LAN ratio of 1:1.6:2) when the lipophilic water-insoluble ingredient, petrolatum, is employed, wherein the ratios are calculated by weight. In other words, a LAN ratio of 1:1.6:2 is equal to 10 g lecithin, 40 g MIRANOL, and 20 g ARASOLVE. Although lecithin is particularly preferred, the amphoteric and nonionic surfactants may vary.

When used as an ingredient in further formulations, the LAN is compatible and generally gives stable milky solutions, lotions, or creams with anionic surfactants such as alkyl sulfates and ethoxylated alkyl sulfates. Other anionic surfactants such as sulfosuccinates may also be used. Typically, LAN compositions are stable and can resist storage at 45° C. for three months or more, which would predict that they have a shelf life at room temperature of at least three years.

In another aspect, the present invention relates to an aqueous delivery or carrier system comprising: at least one organic phospholipid capable of forming bilayers in aqueous solution, at least one amphoteric surfactant, at least one nonionic surfactant preferably present in an amount greater than or equal to the amount of the phospholipid, at least one suspending agent, at least one lipophilic ingredient, and an aqueous phase. The phospholipid, amphoteric surfactant, and nonionic surfactant are present in a combined amount sufficient to allow the lipophilic ingredients to be incorporated into the aqueous delivery system. The amount sufficient to incorporate and maintain a stable system may vary depending on the type of composition; for example, shampoo and mascara formulations may require a lower concentration of LAN than do conditioner, deep treatment, bleach, permanent wave, dye, and relaxant compositions. The suspending agent is present in an amount effective for maintaining a stable system. This amount too may vary depending on the specific make-up of LAN and the particular lipophile(s) used.

The combined amount of organic phospholipid, amphoteric surfactant, and nonionic surfactant used in the composition or delivery system of the invention is preferably equal to or above 1 percent by weight relative to the weight of the delivery system. The preferred phospholipid, lecithin, is preferably used in an amount greater than 0 to about 5% by weight of the delivery system and more preferably in an amount greater than 0 to about 3% by weight of the delivery system. Since lecithin itself is not a pure raw material and may have free glycerides, glycerin, fatty acids, and soaps, adjustments in this ratio may need to be made, i.e., one source of lecithin may require, different ratios of amphoteric and nonionic surfactants than another in order to maximize incorporation of lipophilic ingredient and stability of the system. Preferably, the composition and system of the invention form a stable solution, suspension, lotion, or cream.

The amphoteric surfactants are preferably present in the composition in an amount greater than 0 to about 25% by weight relative to the weight of the delivery system. When the phospholipid/amphoteric/nonionic system is employed as a carrier for a lipophilic material, the amphoteric surfactants are preferably present in the composition in an amount greater than 0 to about 15% by weight relative to the weight of the delivery system.

The nonionic surfactant is preferably present in an amount greater than 0 to about 20% by weight relative to the weight of the delivery system. More preferably, the nonionic surfactant is present in an amount greater than 0 to about 15% by weight relative to the weight of the delivery system.

The suspending agents are preferably present in the composition in an amount ranging from about 1% to 20% by weight relative to the total weight of the delivery system. However, the amount of suspending agent will depend on the viscosity increasing properties of the particular suspending agent. More preferably, the suspending agents are present in an amount ranging from about 1% to about 10% by weight. Preferably, one of ordinary skill in the art will be able to determine routinely the preferred amount of suspending agent depending on the specific LAN delivery system and the application envisaged. The suspending agent is added in an amount effective for maintaining a stable composition or stable system. As defined above, a stable composition or system is one that does not experience substantial settling out or substantial phase separation.

Lipophilic "ingredients" or "materials" or other water-insoluble materials include, but are not limited to hydrocarbons, waxes, silicones, oil-soluble vitamins such as Vitamin E and Vitamin A, sunscreens, ceramides and natural oils. The lipophilic ingredients may be in the form of sunscreens, bacteriostats, moisturizers, colors, topical pharmaceuticals and the like. Preferred lipophilic ingredients include: petrolatum, polyethylenes, beeswax, Vitamin E, Vitamin E Acetate, Vitamin A Palmitate, olive oil, mineral oil, 2-oleamido-1,3-octadecanediol, octylmethoxy cinnamate, octyl salicylate, and silicones such as siloxanes, dimethicone, cyclomethicone, phenyl trimethicone, dimethiconol, dimethicone copolyol, and laurylmethicone copolyol. The lipophilic ingredients can, for example, moisturize or condition the skin, hair, and/or eyelashes and leave behind no oily feel.

The aqueous phase of the inventive delivery system can contain additional ingredients such as anionic surfactants, organic salts, inorganic salts, proteins, hair dyes, water-soluble polymers, quaternary ammonium compounds, complex and simple carbohydrates, amino acids, preservatives and fragrances.

If the inventive system is to be used in concentrated form, i.e., with about 5% by weight of the organic phospholipid and greater than 1% of added lipophilic ingredient, the composition preferably has a pH ranging from 4–12 for maximum stability. The more concentrated the solution, the better the delivery. In the present invention, the amount of lipophilic ingredient preferably ranges from about 0.1% to about 50% by weight relative to the weight of the delivery system.

If this blend is diluted with water or the blend is used as an ingredient in another composition, then the pH has a broader range, i.e., preferably ranges from 2–12, and a wider variety of additives can be included in the solution. These dilute blends canstill bevery effective in delivering lipophilic ingredients.

Another embodiment of the present invention is drawn to a process for preparing the aqueous system of the present invention. This process comprises: (a) combining the following ingredients to obtain a mixture: at least one organic phospholipid capable of forming bilayers in aqueous solution, at least one amphoteric surfactant, at least one nonionic surfactant, at least one lipophilic agent, and water, where the nonionic surfactant is present in an amount by weight equal to or greater than the amount of the organic phospholipid, (b) heating and stirring the combined ingredients of (a), and (c) adding an effectiveamount of suspending agent and stirring with additional heating. Either a high shear apparatus or a normal mechanical stirrer may be used for the stirring.

The mixture is preferably heated at a temperature of 65° C. to 85° C. in step (b), depending on the melting points of the solid surfactants. Still more preferably, the mixture is heated to about 70° C.

More specifically, the preparation of the carrier system of the present invention may be carried out as follows. Lecithin (L) is dispersed in water. The lipophilic material is combined with nonionic surfactant(s) (N) at appropriate ratios and added to the lecithin/water dispersion. An amphoteric surfactant (A) is added and the mixture is heated, while being stirred for about 15 minutes at about 70° C. An effective amount of suspending agent is subsequently added and the solution stirred at about 70° C. for an additional 10 minutes. The combination of these ingredients results in a stable, milky system that is referred to as the LAN delivery system which can then be used as a "raw material" to make finished products.

In another embodiment, the present invention is drawn to a method for treating keratinous substances such as, but not limited to, hair, skin, or eyelashes. First an aqueous solution is prepared containing:

- at least one organic phospholipid capable of forming bilayers in aqueous solution;
- at least one amphoteric surfactant;
- at least one nonionic surfactant present in an amount by weight equal to or greater than the amount of the phospholipid;
- at least one lipophilic ingredient;
- and at least one suspending agent.

The phospholipid, amphoteric surfactant, and nonionic surfactant are present in a combined amount sufficient to allow the lipophilic ingredient to be incorporated into the aqueous solution. The suspending agent is present in an amount effective for maintaining a stable system. The milky LAN system is then applied to the keratinous substances. The term "treating" in the context of this invention includes, but is not limited to, shampooing, conditioning, dyeing, bleaching, permanent waving, relaxing, setting, moisturizing, and making-up, for example, applying mascara or foundation.

As mentioned previously, the composition and carrier system of the present invention can be used as an ingredient itself in, for example, shampoos, conditioners (rinse-off and leave-in), deep treatments for hair, body washes, bath gels, hair dyeing compositions, permanent wave formulations, relaxers, make-up preparations, particularly mascara and foundation, and skin creams or lotions.

With respect to hair products, the carrier system of the present invention can be used to formulate hair products, e.g., for normal hair, color-treated hair, dry hair, fine hair, and damaged hair. For each type of hair, the LAN delivery system can be used to create a regimen comprising shampoo, conditioner, and deep treatment, (i.e., deep conditioner). Additional nonionic, amphoteric, and also anionic surfactants can be added to the LAN delivery system. In general, the concentration of the LAN delivery system is increased within each regimen from shampoo to conditioner to deep treatment. Thus, the deep treatment formulations may have the most concentrated hydrophobe-carrying LAN.

The LAN systems of the invention can be further associated, in the hair products described above, with proteins including hydrolyzed soy protein, lauryldimonium hydrolyzed soy protein (cationic Soya protein) and wheat amino acids. The proteins could also include corn, wheat, milk, or silk proteins, collagens, keratins, or others. Furthermore, taurine and arginine hydrochloride may be associated therein to maximize protein binding to the hair. Cationic proteins or proteins in general may be stabilizers for the LAN delivery system and enhance its delivery by changing the charge on the surface of the LAN structure. The skin and the hair attract cationic ingredients, and proteins are generally substantive to these tissues.

In conditioning emulsions, nonionic emulsifiers such as glyceryl stearate and PEG-100 stearate can be used, and the LAN delivery system is treated as a water-insoluble, particularly a lipophilic, ingredient itself.

Other ingredients in the LAN delivery system hair care compositions may include cationic polymers, such as polyquaternium 4, polyquaternium 6, polyquaternium 7, polyquaternium 10, polyquaternium 11, polyquaternium 16, polyquaternium 22, and polyquaternium 32, cationic conditioners, such as quaternium 27, behenamidopropyl PG-dimonium chloride, hydroxyethyl tallowdimonium chloride, hexadimethrine chloride, stearalkonium chloride, and cetrimonium chloride; isoparaffins; sodium chloride; propylene glycol; preservatives such as phenoxyethanol, methylparaben, ethylparaben, and propylparaben; pH adjusters such as phosphoric acid; humectants such as trehalose; and emollients such as octyldodecanol. Many other examples of materials from the classes listed above would be readily known to one of ordinary skill in the art.

Further, shampoos, conditioners, and deep treatments within the scope of the present invention may be used on hair which has been treated, e.g., with color (dye or bleach) or chemicals (permanent wave or straightening), or which is dry or fine and show significant substantivity for the hair.

The invention will be further clarified by the following examples, which are intended to be illustrative of the invention, but not limiting thereof.

EXAMPLES

Example 1

Study Using LAN with the Lipophilic Material Petrolatum

The following example illustrates the use of LAN to incorporate the lipophilic ingredient petrolatum into an aqueous system. Petrolatum is a highly desirable component in numerous skin and hair care products because of its moisturizing and protecting properties. However, because of its hydrophobic nature, petrolatum has previously been difficult to formulate in an aqueous environment without phase separation.

A LAN composition comprising lecithin (L), MIRANOL C2M-SF Conc. (A), ARLASOLVE 200 (Iso-Ceteth-20) (N), and the suspending agent, SEPIGEL 305 (Polyacrylamide/C13–14 Isoparaffin/Laureth 7) from SEPPIC Inc, was used to incorporate White Fonoline, a petrolatum from Witco Petroleum Specialties, into a LAN delivery system. Table 1 shows that stable lotions of lipophilic agents can be achieved in systems that contain as low as 1.75% by weight of the lecithin, amphoteric surfactant, and nonionic surfactant, relative to the total weight of the delivery system. The LAN ratio was maintained at 1:1.6:2.

TABLE 1

Varying amounts of LAN used to incorporate petrolatum into an aqueous system.

| L Lecithin (g) | A MIRANOL* (g) | N ARLASOLVE (g) | White Fonoline (Petrolatum) (g) | Sepigel 305 (g) | Water (g) | Result | % LAN |
|---|---|---|---|---|---|---|---|
| 0.25 | 1 | 0.5 | 16 | 2 | 80.25 | Stable lotion | 1.75 |
| 0.5 | 2 | 1 | 16 | 2 | 78.5 | Stable lotion | 3.5 |

TABLE 1-continued

Varying amounts of LAN used to incorporate petrolatum into an aqueous system.

| L Lecithin (g) | A MIRANOL* (g) | N ARLASOLVE (g) | White Fonoline (Petrolatum) (g) | Sepigel 305 (g) | Water (g) | Result | % LAN |
|---|---|---|---|---|---|---|---|
| 1 | 4 | 2 | 16 | 2 | 75 | Stable lotion | 7 |
| 2 | 8 | 4 | 4 | 6 | 76 | Stable lotion | 14 |

*MIRANOL C2M-SF Conc. contains about 40% amphoteric surfactant.

Example 2
Comparison of Increasing Amounts of Petrolatum Incorporated by the LAN System Similar to example 1 above, a LAN delivery system was prepared with the following ingredients: lecithin (L), MIRANOL C2M-SF Conc. (A), ARLASOLVE 200 (N), the suspending agent, SEPIGEL 305, and White Fonoline. Stable systems of the petrolatum/LAN delivery system that contain from 4% to 50% petrolatum were accomplished while maintaining a LAN ratio of 1:1.6:2 (This is because 1 g MIRANOL C2M-SF Conc. is approximately 0.4 g of amphoteric surfactant.). See Table 2. As the experiments demonstrate, the loads of the following LAN systems may be greater than 100% and as high as 50 times the amount of phospholipid present. As is evidenced by the examples of Table 2, the skilled artisan may be required to vary the amount LAN ratio or adjust the amount of suspending agent in order to obtain a stable system.

TABLE 2

Increasing amounts of petrolatum incorporated into a LAN delivery system.

| L Lecithin (g) | A MIRANOL (g) | N ARLASOLVE (g) | White Fonoline (g) | Sepigel 305 (g) | Water (g) | Results |
|---|---|---|---|---|---|---|
| 2 | 8 | 4 | 4 | 2 | 80 | Unstable |
| 2 | 8 | 4 | 4 | 4 | 78 | Stable solution |
| 2 | 8 | 4 | 6 | 4 | 76 | Stable lotion |
| 2 | 8 | 4 | 8 | 4 | 74 | Stable lotion |
| 1 | 4 | 2 | 8 | 2 | 83 | Unstable |
| 1 | 4 | 2 | 16 | 2 | 75 | Stable lotion |
| 1 | 4 | 2 | 25 | 2 | 66 | Stable lotion |
| 1 | 4 | 2 | 50 | 4 | 39 | Unstable |
| 1 | 4 | 2 | 50 | 6 | 37 | Stable cream |

Example 3
Study Varying the Amount of Suspending Agent in the LAN System

The compositions of Example 1 and 2 were utilized to study the effect of varying the amount of suspending agent in a LAN delivery system that incorporates petrolatum. As reflected in Table 3, one of ordinary skill in the art would routinely vary the amount of suspending agent in order to maintain a stable, milky system. Table 3 illustrates the amount of suspending agent needed to incorporate petrolatum into a stable, milky system using different amounts of lecithin, amphoteric surfactant, and nonionic surfactant. In each example, an unstable LAN delivery system was stabilized by the addition of more suspending agent. Up to 15% of the suspending agent was used in the LAN milks.

TABLE 3

LAN delivery systems with varying amounts of suspending agent.

| L Lecithin (g) | A MIRANOL (g) | N ARLASOLVE (g) | White Fonoline (g) | Sepigel 305 (g) | Water (g) | Results |
|---|---|---|---|---|---|---|
| 1 | 4 | 2 | 16 | 2 | 75 | Unstable |
| 1 | 4 | 2 | 8 | 2 | 83 | Stable lotion |
| 1 | 4 | 2 | 8 | 4 | 81 | Stable lotion |
| 2 | 8 | 4 | 4 | 2 | 80 | Unstable |
| 2 | 8 | 4 | 4 | 6 | 76 | Stable lotion |
| 1 | 4 | 2 | 50 | 2 | 41 | Unstable |
| 1 | 4 | 2 | 50 | 4 | 39 | Unstable |
| 1 | 4 | 2 | 50 | 6 | 37 | Stable lotion |
| 1 | 4 | 2 | 20 | 15 | 58 | Stable lotion |

Example 4
Use of LAN Compositions to Incorporate Silicones

Silicones are highly desirable ingredients to enhance shine and softness but are difficult to formulate because of their inherent insolubility in water and alcohol. The following example illustrates the use of a LAN composition to incorporate silicones into an aqueous system. The amount of lecithin (L), MIRANOL C2M-SF Conc. (A), and ARLASOLVE 200 (Iso-Ceteth-20) (N), remained constant while the amount and type of suspending agent were varied. The suspending agents utilized include: AMIGEL, a sclerotium gum available from Alban Muller; CELLOSIZE QP 4400, a hydroxyethylcellulose available from Amerchol; CROTHIX, a PEG-150 Pentaerythrityl Tetrastearate available from Croda.

The resulting LAN compositions were able to incorporate the following silicones into a stable, milky delivery system as described in Table 4:

DC 1411: Octamethylcyclotetrasiloxane from Dow Corning;

DC Q2-5200: Silicone glycol/dodecene from Dow Corning;

DC 1402: Decamethylcyclopentasiloxane from Dow Corning; and

DC 200: Polydimethylsiloxane 60,000 cSt (centistokes) from Dow Corning.

TABLE 4

Incorporation of silicones into LAN delivery systems.

| L Lecithin (g) | A MIRANOL (g) | N ARLASOLVE (g) | Silicone (g) | Suspending Agent (g) | Water (g) | Results |
|---|---|---|---|---|---|---|
| 1 | 4 | 2 | DC 1411, 10 | Sepigel 305, 3 | 80 | Stable lotion |
| 1 | 4 | 2 | DC Q2-5200, 10 | Amigel, 1 | 82 | Stable solution |
| 1 | 4 | 2 | DC 1402, 15 | Cellosize, 3 | 75 | Stable lotion |
| 1 | 4 | 2 | DC 200, 5 | Crothix, 5 | 83 | Stable lotion |

Example 5
Use of LAN Compositions to Incorporate Various Lipophilic Ingredients

LAN compositions have been utilized to formulate a variety of LAN delivery systems that incorporate a variety of lipophilic ingredients. Additionally, it is within the routine experimentation of the skilled artisan to vary the lipophilic ingredient or the suspending agent in order to produce a stable, milky LAN system. Table 5 reveals the use of different lipophilic agents as well as different suspending agents that were used to make stable LAN delivery systems.

In Table 5, the LAN composition was composed of lecithin (L), MIRANOL C2M-SF Conc. (A), ARLASOLVE 200 (Iso-Ceteth-20) (N), and a variety of suspending agents including CROTHIX, SEPIGEL, and BENTOLITE WH, a bentonite clay from Southern Clay Products. The LAN compositions were used to incorporate several lipophilic ingredients in addition to White Fonoline including: VERSAFLOW, a liquid polyethylene from Shamrock; Beeswax from Kostner Keunen, Inc.; and Diglyceride, a vegetable diglyceride from Kostner Keunen, Inc.

TABLE 5

Examples of various LAN delivery systems.

| L Lecithin (g) | A MIRANOL (g) | N ARLASOLVE (g) | Lipophile (g) | Suspending Agent (g) | Water (g) | Results |
|---|---|---|---|---|---|---|
| 2 | 8 | 4 | Versaflow, 4 | Sepigel, 4 | 78 | Stable lotion |
| 2 | 8 | 4 | Beeswax, 4 | Sepigel, 4 | 78 | Stable lotion |
| 2 | 8 | 4 | White Fonoline, 4 | Bentolite WH, 2 | 80 | Stable lotion |
| 2 | 8 | 4 | White Fonoline, 4 | Bentolite WH, 6 | 76 | Stable lotion |
| 1 | 4 | 2 | Diglyceride, 5 | Crothix, 3 | 85 | Stable lotion |

Example 6
Preparation of Hair Relaxer Containing a Milky LAN System

The following hair relaxer was formulated from a LAN delivery system that incorporated petrolatum. All the ingredient amounts are shown in weight percent.

| Lecithin | 1.0% |
|---|---|
| Miranol C2M-SF | 4.0% |
| Arlasolve 200 | 2.0% |
| White Fonoline | 20.0% |
| Sepigel 305 | 15.0% |
| Sodium Hydroxide | 2.5% |
| Water | 55.5% |

The resulting hair relaxer cream was applied to six swatches of kinked hair at room temperature. The hair swatches were then rinsed with water. Following shampooing with 10% Sodium Laureth Sulfate (SLES), each of the six swatches wasalmost 98% relaxed. The relaxed hair swatches were also notably soft.

Example 7
Use of a Milky LAN/Petrolatum System in Hair Care

The superior moisturizing and protecting properties of petrolatum offermany advantages for use in hair care. The following hair care treatment was formulated using a LAN/Petrolatum delivery system. All the ingredient amounts are shown in weight percent.

| Lecithin | 1.0% |
|---|---|
| Miranol C2M-SF | 4.0% |
| Arlasolve 200 | 2.0% |
| White Fonoline | 8.0% |
| Sepigel 305 | 4.0% |
| Water | 81.0% |

The resulting LAN/Petrolatum lotion was applied to bleached hair and relaxed hair for 5 minutes at room temperature then rinsed with warm water. The treated hair was moist and had improved softness.

Example 8
Use of a Milky LAN/Silicone System in Hair Care

Similar to petrolatum, silicones offer superior moisturizing and protecting properties that are desirable for many hair and skin care applications. The following hair care treatment was formulated using a LAN/silicone delivery system. All the ingredient amounts are shown in weight percent.

| Lecithin | 1.0% |
|---|---|
| Miranol C2M-SF | 4.0% |
| Arlasolve 200 | 2.0% |
| DC 1411 | 10.0% |
| Sepigel 305 | 3.9% |
| Water | 80.0% |

The resulting LAN/silicone lotion was applied to hair for 5 minutes at room temperature then rinsed with warm water. The treated hair felt soft, was easy to detangle, and had increased shine.

What is claimed is:
1. A composition comprising:
   at least one phospholipid capable of forming bilayers in aqueous solution;
   at least one amphoteric surfactant;
   at least one nonionic surfactant present in an amount by weight equal to or greater than the amount of said at least one phospholipid; and
   at least one suspending agent present in an amount effective for maintaining a stable composition, wherein said at least one phospholipid and said at least one amphoteric surfactant are present in a ratio of 1:0.8 and above.

2. A composition according to claim 1, wherein said composition further comprises water.

3. A composition according to claim 1, wherein said at least one nonionic surfactant is present in an amount by weight greater than the amount of said at least one phospholipid.

4. A composition according to claim 1, wherein said at least one amphoteric surfactant is present in an amount by weight greater than the amount of said at least one phospholipid.

5. A composition according to claim 1, wherein said at least one phospholipid capable of forming bilayers in aqueous solution is a lecithin.

6. A composition according to claim 1, wherein said composition further comprises at least one lipophilic ingredient.

7. A composition according to claim 6, wherein said at least one lipophilic ingredient is selected from hydrocarbons, waxes, and silicones.

8. A composition according to claim 7, wherein said hydrocarbons are selected from petrolatum and polyethylenes.

9. A composition according to claim 7, wherein said silicones include siloxane.

10. A composition according to claim 1, wherein said at least one suspending agent is selected from biopolymers, polysaccharide gums, polyacrylamides, stearates, and inorganic clays.

11. A composition according to claim 1, wherein said at least one nonionic surfactant contains at least one group selected from $C_8$ to $C_{24}$ fatty alcohol, $C_8$ to $C_{24}$ fatty acid, and $C_8$ to $C_{24}$ glyceride.

12. A composition according to claim 1, wherein said at least one nonionic surfactant has an HLB of at least 10.

13. A composition according to claim 1, wherein said at least one amphoteric surfactant is selected from betaines, sultaines, hydroxysultaines, alkyl amphodiacetates, alkyl amphodipropionates, imidazolines, and salts thereof.

14. A composition according to claim 13, wherein said at least one amphoteric surfactant is selected from cocamphodipropionate and cocamidopropyl hydroxysultaine.

15. A composition according to claim 1, wherein said at least one phospholipid, said at least one amphoteric surfactant, and said at least one nonionic surfactant are present in a ratio of 1:0.8:2 and above.

16. A composition according to claim 1, wherein said at least one phospholipid, said at least one amphoteric surfactant, and said at least one nonionic surfactant are present in a ratio of 1:1.2:2 and above.

17. A composition according to claim 16, wherein said at least one phospholipid, said at least one amphoteric surfactant, and said at least one nonionic surfactant are present in a ratio of 1:1.6:2 and above.

18. A delivery system for lipophilic ingredients comprising:
   at least one phospholipid capable of forming bilayers in aqueous solution;
   at least one amphoteric surfactant;
   at least one nonionic surfactant present in an amount by weight equal to or greater than the amount of said at least one phospholipid;
   at least one suspending agent present in an amount effective for maintaining a stable delivery system;
   at least one lipophilic ingredient; and
   an aqueous phase,
   wherein said at least one phospholipid, said at least one amphoteric surfactant, and said at least one nonionic surfactant are present in a combined amount sufficient to allow said at least one lipophilic ingredient to be incorporated into said system, and wherein said at least one phospholipid and said at least one amphoteric surfactant are present in a ratio of 1:0.8 and above.

19. A delivery system according to claim 18, wherein said delivery system is a stable solution, suspension, lotion, or cream.

20. A delivery system for lipophilic ingredients according to claim 18, wherein said at least one amphoteric surfactant is present in an amount by weight greater than the amount of said at least one phospholpid and wherein said at least one nonionic surfactant is present in an amount by weight equal to or greater than the amount of said at least one phospholipid.

21. A delivery system according to claim 18, wherein said aqueous phase further comprises additional ingredients selected from anionic surfactants, organic salts, inorganic salts, proteins, hair dyes, water-soluble polymers, and amino acids.

22. A delivery system according to claim 18, wherein said at least one lipophilic ingredient is selected from hydrocarbons, waxes, and silicones.

23. A delivery system according to claim 22, wherein said at least one lipophilic ingredient is selected from hydrocarbons.

24. A delivery system according to claim 23, wherein said hydrocarbons are selected from petrolatum and polyethylenes.

25. A delivery system according to claim 22, wherein said silicones include siloxane.

26. A delivery system according to claim 18, wherein said at least one suspending agent is selected from biopolymers, polysaccharide gums, polyacrylamides, stearates, and inorganic clays.

27. A delivery system according to claim 18, wherein said suspending agent is present in an amount of 1% to 20% by weight relative to the total weight of the delivery system.

28. A delivery system according to claim 27, wherein said suspending agent is present in an amount of 1% to 10% by weight relative to the total weight of the delivery system.

29. A delivery system according to claim 18, wherein said at least one phospholipid capable of forming bilayers in aqueous solution is a lecithin.

30. A delivery system according to claim 18, wherein said at least one nonionic surfactant contains at least one group selected from $C_8$ to $C_{24}$ fatty alcohol, $C_8$ to $C_{24}$ fatty acid, and $C_8$ to $C_{24}$ glyceride.

31. A delivery system according to claim 18, wherein said at least one nonionic surfactant has an HLB of at least 10.

32. A delivery system according to claim 18, wherein said at least one amphoteric surfactant is selected from betaines, sultaines, hydroxysultaines, alkyl amphodiacetates, alkyl amphodipropionates, imidazolines, and salts thereof.

33. A delivery system according to claim 32, wherein said at least one amphoteric surfactant is selected from cocamphodipropionate and cocamidopropyl hydroxysultaine.

34. A delivery system according to claim 28, wherein said at least one phospholipid is present in an amount of greater than 0 to 5% by weight relative to the total weight of said delivery system.

35. A delivery system according to claim 34, wherein said at least one phospholipid is present in an amount of greater than 0 to 3% by weight relative to the total weight of said delivery system.

36. A delivery system according to claim 18, wherein said at least one amphoteric surfactant is present in an amount greater than 0 to 25% by weight relative to the total weight of the delivery system.

37. A delivery system according to claim 36, wherein said at least one amphoteric surfactant is present in an amount greater than 0 to 15% by weight relative to the total weight of the delivery system.

38. A delivery system according to claim 18, wherein said at least one nonionic surfactant is present in an amount greater than 0 to 20% by weight relative to the total weight of the delivery system.

39. A delivery system according to claim 38, wherein said at least one nonionic surfactant is present in an amount greater than 0 to 15% by weight relative to the total weight of the delivery system.

40. A delivery system according to claim 18, wherein said at least one phospholipid, said at least one amphoteric surfactant, and said at least one nonionic surfactant are present in a ratio of 1:0.8:2 and above.

41. A delivery system according to claim 18, wherein said at least one phospholipid, said at least one amphoteric surfactant, and said at least one nonionic surfactant are present in a ratio of 1:1.2:2 and above.

42. A delivery system according to claim 41, wherein said at least one phospholipid, said at least one amphoteric surfactant, and said at least one nonionic surfactant are present in a ratio of 1:1.6:2 and above.

43. A delivery system according to claim 18, wherein said at least one phospholipid is a lecithin, said at least one amphoteric surfactant is disodium cocamphodipropionate, and said at least one nonionic surfactant is selected from PPG-5Ceteth-20, PEG-20 Isocetyl Ether, and Oleth-10.

44. A delivery system according to claim 18, wherein said system is in the form of a shampoo, a conditioner, a deep treatment for hair, a body wash, a bath gel, a bath oil, a hair dyeing composition, a permanent wave formulation, a make-up composition, a skin cream, or a lotion.

45. A delivery system according to claim 44, wherein said make-up composition is a mascara or a foundation.

46. A method for the preparation of a delivery system as claimed in claim 18, said method comprising:
(a) combining said at least one phospholipid, said at least one amphoteric surfactant, said at least one nonionic surfactant; said at least one lipophilic ingredient and water to obtain a mixture;
(b) heating and stirring the mixture obtained in step (a);
(c) adding an effective amount of said at least one suspending agent; and
(d) heating and stirring the mixture obtained in step (c).

47. A method for treating a keratinous substance, said method comprising:
preparing a delivery system comprising
at least one phospholipid capable of forming bilayers in aqueous solution;
at least one amphoteric surfactant;
at least one nonionic surfactant present in an amount by weight equal to or greater than the amount of said at least one phospholipid; and
at least one suspending agent present in an amount effective for maintaining a stable delivery system and at least one lipophilic ingredient,
wherein said at least one phospholipid, said at least one amphoteric surfactant, and said at least one nonionic surfactant are present in a combined amount sufficient to allow said lipophilic ingredient to be incorporated into said delivery system, and wherein said at least one phospholipid and said at least one amphoteric surfactant are present in a ratio of 1:0.8 and above; and
applying said delivery system to said keratinous substance.

48. A method according to claim 47, wherein said treating comprises a treatment selected from shampooing, conditioning, dyeing, bleaching, permanent waving, relaxing, setting, moisturizing, and making-up.

49. A method according to claim 47, wherein said keratinous substance is selected from hair, skin, and eyelashes.

50. A method according to claim 48, wherein making-up comprises a treatment selected from applying mascara to the eyelashes and applying foundation to facial skin.

51. A hair relaxing composition comprising:
at least one phospholipid capable of forming bilayers in aqueous solution;
at least one amphoteric surfactant;
at least one nonionic surfactant present in an amount by weight equal to or greater than the amount of said at least one phospholipid;
at least one suspending agent present in an amount effective for maintaining a stable composition;
at least one lipophilic ingredient, wherein said lipophilic ingredient is petrolatum;
sodium hydroxide; and
water,
wherein said at least one phospholipid, said at least one amphoteric surfactant, and said at least one nonionic surfactant are present in a combined amount sufficient to allow said at least one lipophilic ingredient to be incorporated into said hair relaxing composition.

52. A hair relaxing composition according to claim 51, wherein said at least one phospholipid capable of forming bilayers in aqueous solution is a lecithin.

53. A hair relaxing composition according to claim 51, wherein said at least one phospholipid, said at least one amphoteric surfactant, and said at least one nonionic surfactant are present in a ratio of 1:1.6:2.

54. A hair relaxing composition according to claim 51, wherein at least one suspending agent is polyacrylamide.

55. A hair relaxing composition according to claim 51, wherein said at least one nonionic surfactant is PEG-20 isocetyl ether.

56. A hair relaxing composition according to claim 51, wherein said at least one amphoteric surfactant is disodium cocamphodipropionate.

57. A hair conditioning composition comprising:
at least one phospholipid capable of forming bilayers in aqueous solution;
at least one amphoteric surfactant;
at least one nonionic surfactant present in an amount by weight equal to or greater than the amount of said at least one phospholipid;
at least one suspending agent present in an amount effective for maintaining a stable composition;
at least one lipophilic ingredient, wherein said lipophilic ingredient is selected from silicones;
sodium hydroxide; and
water,
wherein said at least one phospholipid, said at least one amphoteric surfactant, and said at least one nonionic surfactant are present in a combined amount sufficient to allow said at least one lipophilic ingredient to be incorporated into said hair conditioning composition.

58. A hair conditioning composition according to claim 57, wherein said at least one phospholipid capable of forming bilayers in aqueous solution is a lecithin.

59. A hair conditioning composition according to claim 57, wherein said at least one phospholipid, said at least one amphoteric surfactant, and said at least one nonionic surfactant are present in a ratio of 1:1.6:2.

60. A hair conditioning composition according to claim 57, wherein at least one suspending agent is polyacrylamide.

61. A hair conditioning composition according to claim 57, wherein said at least one nonionic surfactant is PEG-20 isocetyl ether.

62. A hair conditioning composition according to claim 57, wherein said at least one amphoteric surfactant is disodium cocamphodipropionate.

63. A hair conditioning composition according to claim 57, wherein said silicones are octamethylcyclotetrasiloxane.

* * * * *

UNITED STATES PATENT AND TRADEMARK OFFICE
CERTIFICATE OF CORRECTION

PATENT NO. : 6,440,456 B1
DATED : August 27, 2002
INVENTOR(S) : Nghi Van Nguyen et al.

It is certified that error appears in the above-identified patent and that said Letters Patent is hereby corrected as shown below:

Title page,
Item [57], ABSTRACT,
Line 13, "akeratinous" should read -- a keratinous --.

Column 16,
Line 14, "phospholpid" should read -- phospholipid --.

Column 17,
Line 33, "PPG-5Ceteth-20" should read -- PPG-5-Ceteth-20 --.

Signed and Sealed this

Eighteenth Day of February, 2003

JAMES E. ROGAN
*Director of the United States Patent and Trademark Office*